United States Patent [19]
Sham

[11] Patent Number: 5,822,821
[45] Date of Patent: Oct. 20, 1998

[54] ELECTRIC TOOTHBRUSH

[75] Inventor: John C. K. Sham, Hong Kong, Hong Kong

[73] Assignee: Pentalpha Enterprises Ltd., Hong Kong

[21] Appl. No.: 585,849

[22] Filed: Jan. 12, 1996

[51] Int. Cl.⁶ .................................................. A46B 13/02
[52] U.S. Cl. .............................................. 15/22.1; 15/23
[58] Field of Search ................... 15/22.2, 22.1, 15/23

[56] References Cited

U.S. PATENT DOCUMENTS

| | | |
|---|---|---|
| 3,278,963 | 10/1966 | Bond ........................................ 15/22.1 |
| 3,562,566 | 2/1971 | Kircher .................................... 15/22.1 |
| 3,577,579 | 5/1971 | Duve ........................................ 15/22.1 |
| 3,685,080 | 8/1972 | Hubner . |
| 3,945,076 | 3/1976 | Sung . |
| 4,134,169 | 1/1979 | Sinclair . |
| 4,149,291 | 4/1979 | Stoltz . |
| 4,175,299 | 11/1979 | Teague, Jr. et al. . |
| 4,275,749 | 6/1981 | Caroli ........................................ 15/23 |
| 4,412,823 | 11/1983 | Sakai et al. . |
| 4,603,448 | 8/1986 | Middleton et al. . |
| 4,630,326 | 12/1986 | Stevens . |
| 4,698,869 | 10/1987 | Mierau et al. . |
| 4,791,945 | 12/1988 | Moriyama . |
| 4,995,131 | 2/1991 | Takeda . |
| 5,020,179 | 6/1991 | Scherer . |
| 5,033,150 | 7/1991 | Gross et al. . |
| 5,068,939 | 12/1991 | Holland . |
| 5,077,855 | 1/1992 | Ambasz . |
| 5,088,145 | 2/1992 | Whitefield . |
| 5,142,723 | 9/1992 | Lustig et al. . |
| 5,165,131 | 11/1992 | Staar . |
| 5,177,826 | 1/1993 | Vrignaud et al. . |
| 5,189,751 | 3/1993 | Giuliani et al . |
| 5,253,382 | 10/1993 | Beny . |
| 5,259,083 | 11/1993 | Stansbury, Jr. . |
| 5,263,218 | 11/1993 | Giuliani et al. . |
| 5,289,604 | 3/1994 | Kressner . |
| 5,301,381 | 4/1994 | Klupt . |
| 5,311,633 | 5/1994 | Herzog et al. . |
| 5,341,534 | 8/1994 | Serbinski et al. . |
| 5,353,460 | 10/1994 | Bauman . |
| 5,359,747 | 11/1994 | Amakasu . |
| 5,383,242 | 1/1995 | Bigler et al. . |

*Primary Examiner*—Randall E. Chin
*Attorney, Agent, or Firm*—Salzman & Levy

[57] ABSTRACT

An electric toothbrush is disclosed which includes an elongate body defining a handle, an elongate housing extending from the body and supporting a brush head at a distal end thereof, a drive shaft rotatably mounted within the housing and connected to the brush head, a motor disposed within the body and including a rotating output shaft, and a transmission assembly adapted to convert the rotational movement of the output shaft into reciprocating rotation of the drive shaft and brush head about a common axis of rotation.

1 Claim, 7 Drawing Sheets

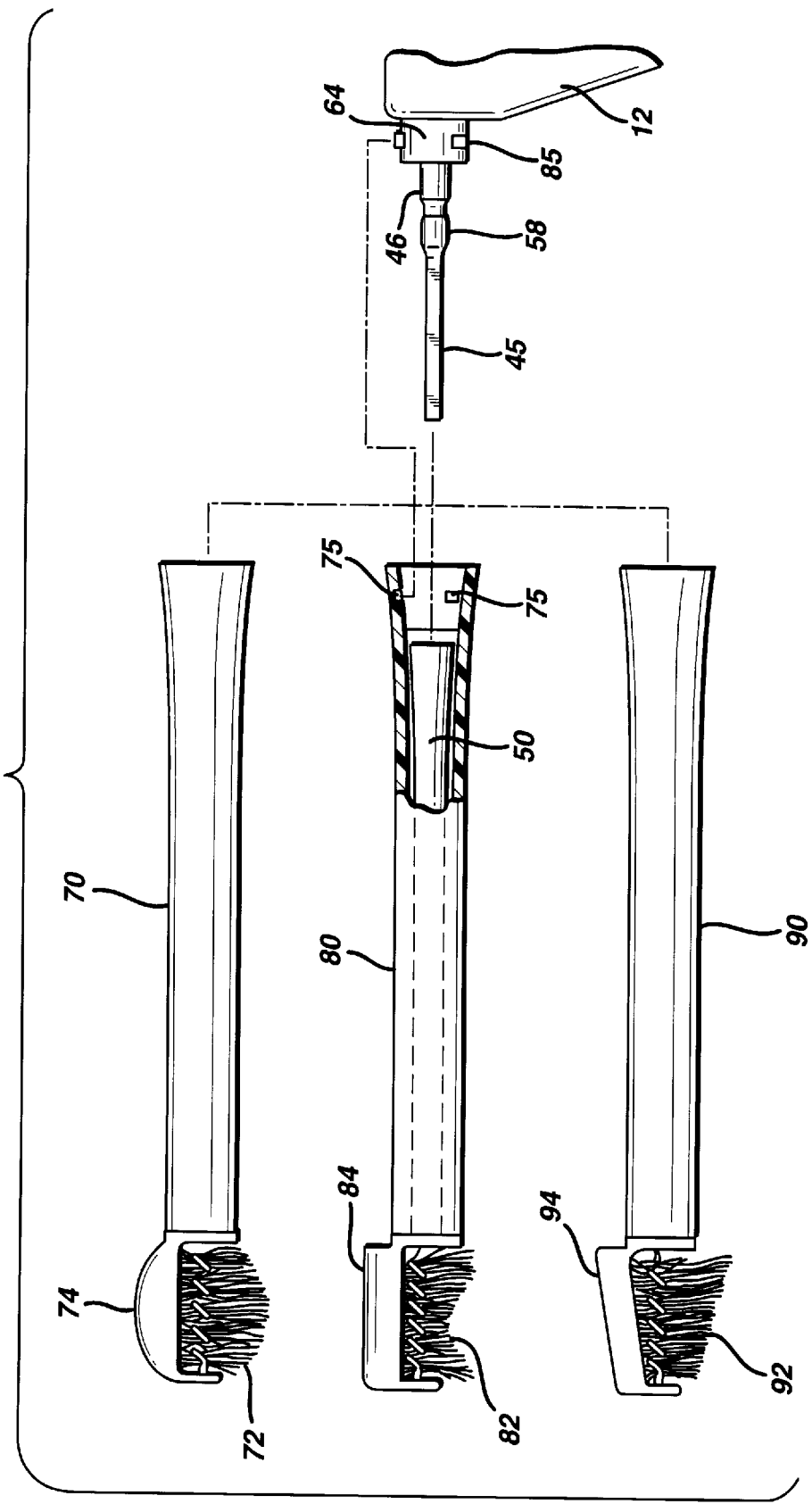

ELECTRIC TOOTHBRUSH

BACKGROUND OF THE INVENTION

1. Field of the Invention

This invention relates to a dental hygiene appliance, and more particularly, to a powered toothbrush having an axially reciprocating brush head driven by an electric motor.

2. Description of the Related Art

Electrically powered toothbrushes are well known in the art. In the past, they have been provided with one or more brush heads that either rotate, oscillate, vibrate or reciprocate about a particular axis of motion depending upon the configuration of their drive mechanism to remove dental plaque thoroughly and quickly. For example, U.S. Pat. No. 5,311,633 to Herzog et al. discloses a power driven toothbrush which includes a brush head mounted to oscillate within an angular sector of rotation. The brush head is driven by a rotating drive shaft connected to a four-bar linkage. The linkage includes a crank and a rocker and the axis of rotation of the brush head is perpendicular to the axis of rotation of the drive shaft. A bevel gear assembly disposed adjacent the brush head translates the motion of the drive shaft to the brush head.

Another example of an electric toothbrush is disclosed in U.S. Pat. No. 5,383,242 to Bigler et al. which includes a motorized drive mechanism consisting of a piston with a lifting cam configured to cause the reciprocating motion of a toothed rack and corresponding rotation of a brush head about an axis perpendicular to the motion of the toothed rack. In the drive assemblies of both Herzog et al. and Bigler et al., a great deal of friction is generated by surface-to-surface contact between rotating components. This friction produces significant power losses and results in low operating efficiencies. To avoid such power losses, the toothbrush of the subject invention is advantageously constructed so that the brush head rotates about the same axis as the drive shaft. Moreover, the subject invention provides a drive assembly with fewer components than prior art toothbrush drive assemblies so that there are fewer surface-to-surface contact points, thereby reducing frictional losses.

SUMMARY OF THE INVENTION

The subject invention is directed to an electric toothbrush for thoroughly and quickly removing dental plaque and debris from and between the teeth and gums. The toothbrush comprises an elongate body defining a handle and having an interior cavity formed therein. An elongate brush support housing extends from a front end of the body and supports a brush head at a distal end thereof. An elongate drive shaft is rotatably supported within the elongate housing and is connected to the brush head. An electric motor is disposed within the interior cavity of the body and it includes a rotating output shaft. The toothbrush further includes a transmission assembly which is disposed within a transmission housing situated in the interior cavity of the body. The transmission assembly is adapted to convert the rotational movement of the output shaft into reciprocating axial rotation of the drive shaft and brush head about a common axis of rotation.

The transmission assembly includes a crank which is operatively connected to the output shaft of the motor and a rocker arm which is operatively connected to the drive shaft disposed in the elongate housing. The crank has a transverse slider projecting from one end thereof and the rocker has an elongate slot formed therein. The transmission assembly further comprises a gear train which includes a driving gear mounted on the output shaft of the motor and a driven gear mounted to the crank. Rotation of the driven gear causes corresponding pendulum-like reciprocating motion of the rocker arm as the slider translates within the slot formed in the rocker arm. A rocker shaft extends from the rocker arm to the drive shaft so that the reciprocating motion of the rocker arm is translated to the brush head.

The electric toothbrush of the subject invention further includes a rechargeable battery system which is disposed within the interior cavity of the body for energizing the electric motor. The battery is preferably charged when the toothbrush is positioned on a base structure which is connected to a source of electrical power.

In a preferred embodiment of the subject invention, the elongate brush support housing is detachably mounted to the front end of the elongate body and the drive shaft is disengagable from the rocker shaft. Preferably, the distal end portion of the elongate brush support housing includes a shroud which is dimensioned and configured to partially enclose the brush head. It is envisioned that the shroud and the brush head can have a variety of complementary geometric configurations, and that a plurality of interchangeable support housings can be provided in a set for use with a single toothbrush body.

These and other features of the toothbrush of the subject invention will become more readily apparent to those skilled in the art from the following detailed description of the invention taken in conjunction with the drawings.

BRIEF DESCRIPTION OF THE DRAWINGS

So that one skilled in the art to which the subject invention appertains will better understand how to make and use the electric toothbrush of the subject invention, preferred embodiments thereof will be described hereinbelow with reference to the drawings wherein:

FIG. 10 illustrates three different brush support housings adapted for detachable engagement with the handle portion of the electric toothbrush of the subject invention.

DETAILED DESCRIPTION OF THE PREFERRED EMBODIMENTS

Figure 1:
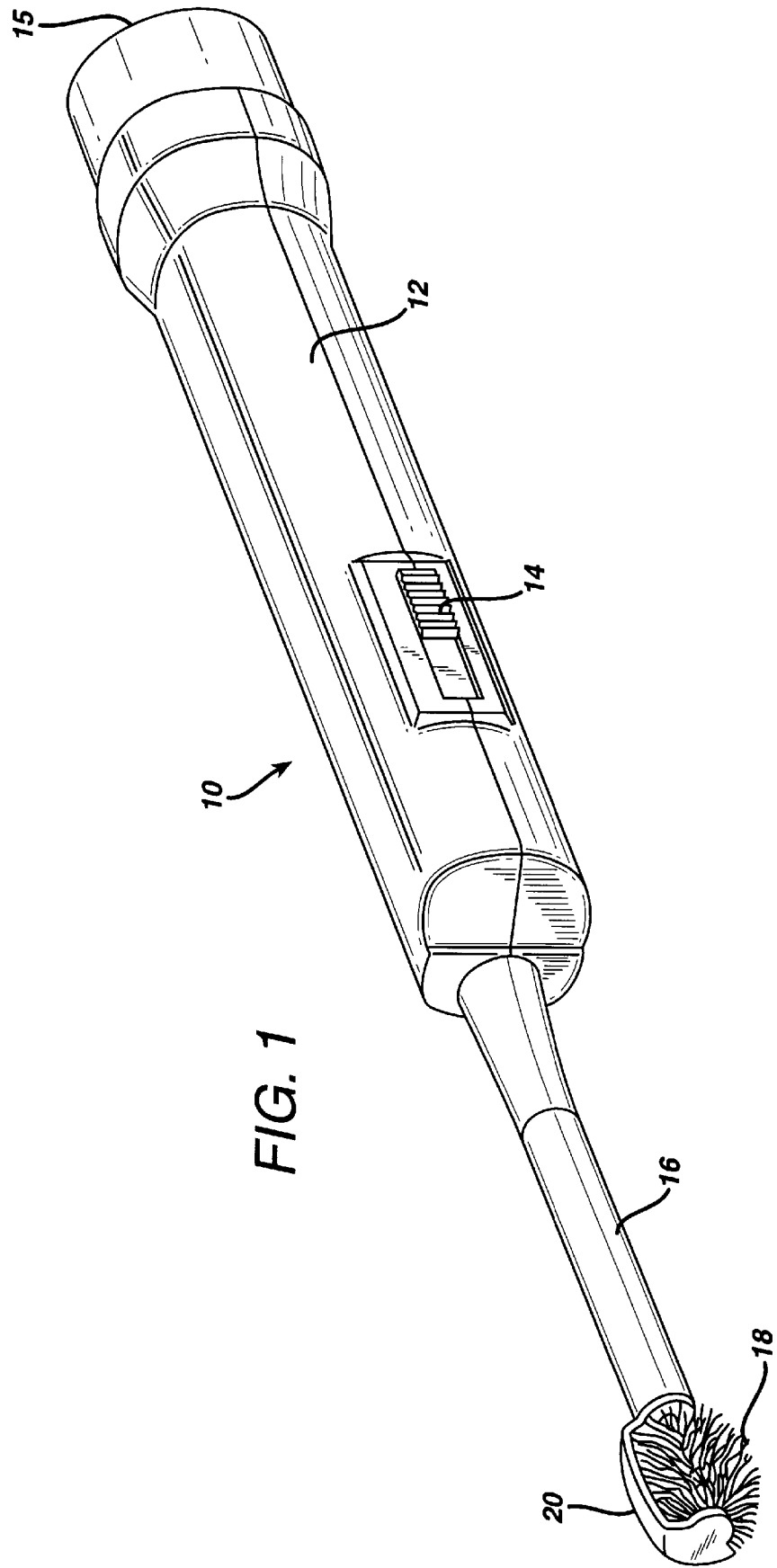
FIG. 1 is a perspective view of an electric toothbrush constructed in accordance with a preferred embodiment of the subject invention.

Referring now to the drawings wherein like reference numerals identify similar structural elements of the subject invention, there is illustrated in FIG. 1 an electric toothbrush constructed in accordance with a preferred embodiment of the subject invention and designated generally by reference numeral 10.

Referring to FIG. 1, the electric toothbrush 10 of the subject invention includes an elongated body portion 12 defining an ergonomic handle for convenient manipulation by a user. Body portion 12 is adapted to be supported in an upright orientation on a base structure (not shown). The base structure will be connected to a source of electrical power and will serve as a source of power for the toothbrush which preferably includes a rechargeable battery system. Such systems are well known to those having ordinary skill in the art. A conventional slidable power switch 14 is provided on body portion 12 for controlling the operation of toothbrush 10, and an electrically conductive end cap 15 is threadably connected to the rear end of body portion 12 to transfer electrical energy from the base to the rechargeable battery disposed within the body portion when the toothbrush is charging.

An elongated brush support housing 16 extends from the front end of body portion 12 for supporting the brush head 18 of toothbrush 10. Brush head 18 is preferably formed by an elongated strand of metal having a multiplicity of radially outwardly projecting bristles disposed along its length that is twisted about its longitudinal axis to form a brush with a multiplicity of individually standing bristles with a central spine. The resulting configuration of the cleaning bristles effectively remove plaque and debris from the gaps and spaces located between teeth. A shroud 20 which may be formed integral with brush support housing 16 encloses a portion of brush head 18. The shroud tends to prevent toothpaste from spraying away from the area of the mouth which is being cleaned, and also serves to protect the area of cheek and gum not intended to be contacted by the moving brush head.

Figure 2:
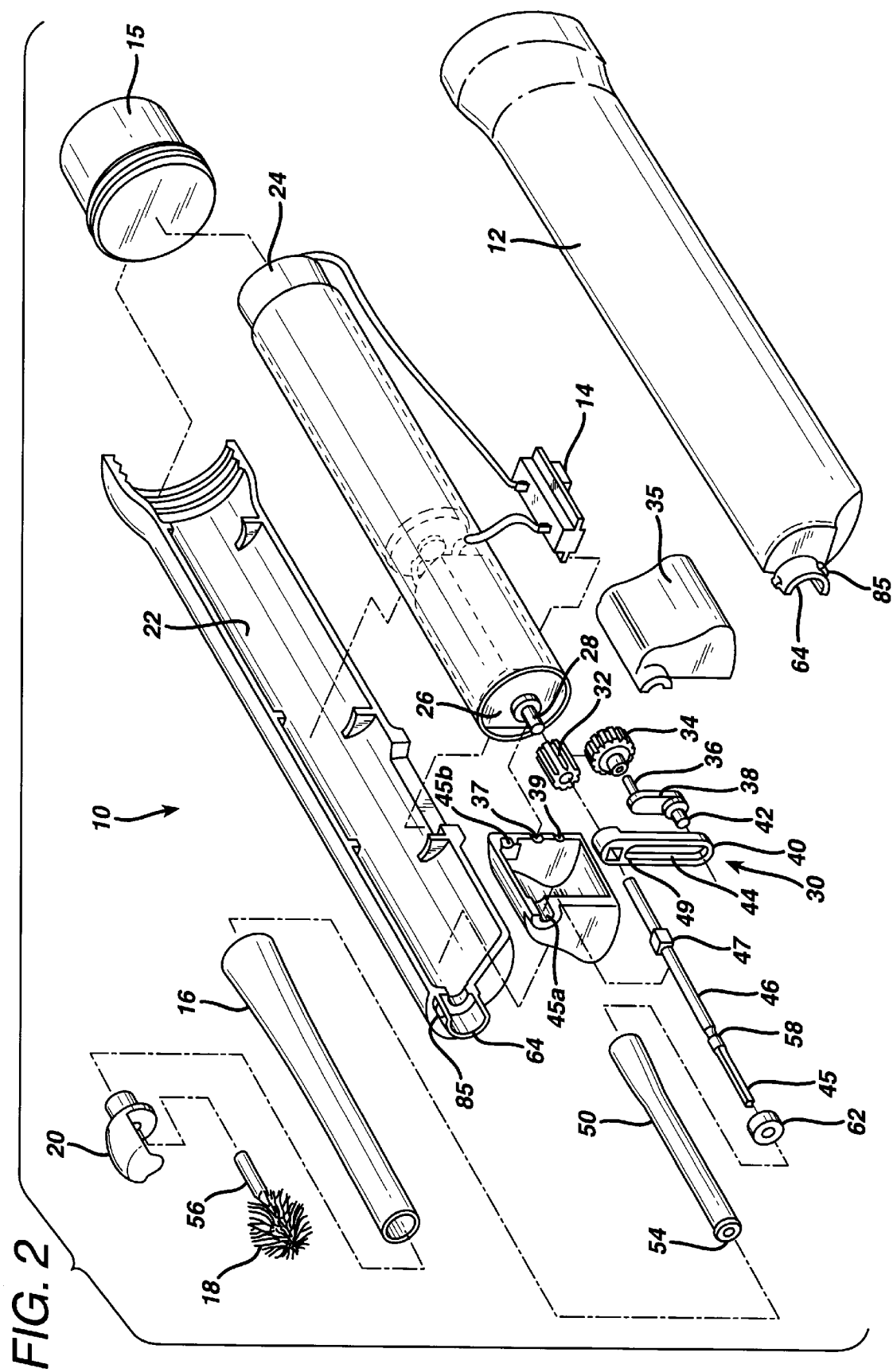
FIG. 2 is an exploded perspective view of the electric toothbrush shown in FIG. 1 with the components thereof separated for ease of illustration.
Figure 3:
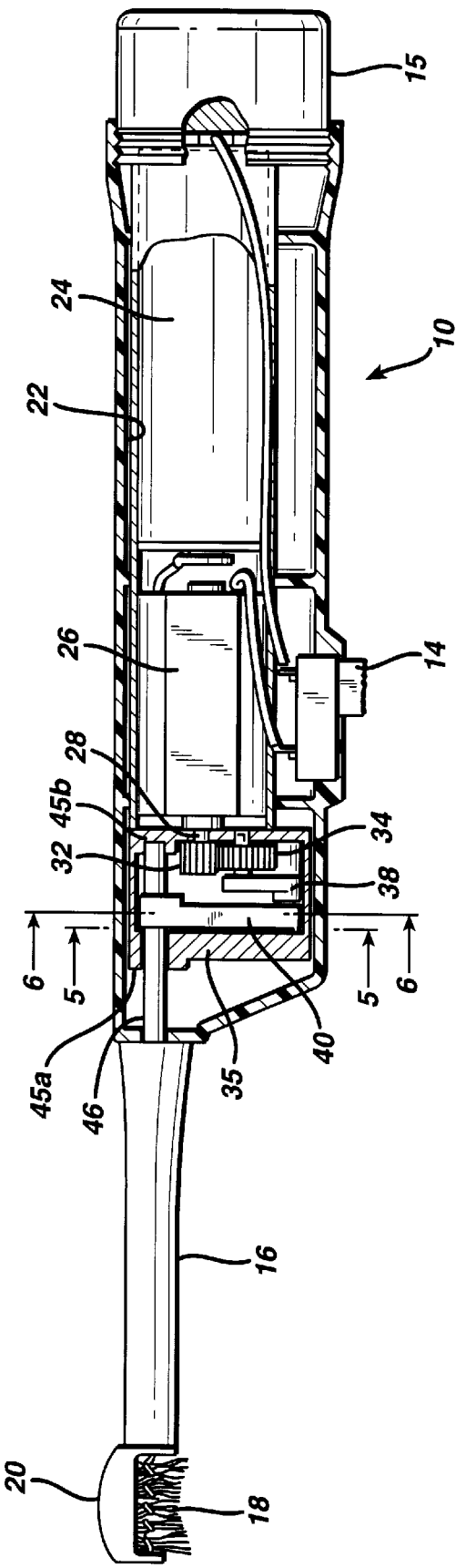
FIG. 3 is a side elevational view in partial cross-section of the electric toothbrush of FIG. 1 illustrating the internal components of the toothbrush housed within the handle portion.

Referring to FIGS. 2 and 3, body portion 12 defines an elongated interior cavity 22 for supporting the various mechanical and electrical components which drive powered toothbrush 10. In particular, a rechargeable battery 24 is disposed within cavity 22 adjacent the rear end thereof and an electric motor 26 is disposed in front of the battery. As illustrated, both the battery and the motor are preferably encased by a thin layer of insulation (i.e., a plastic wrap). The rechargeable battery may be a nickel-cadmium type battery or the like. The motor is preferably a conventional D.C. motor having an armature. Conductive wires connect battery 24 and motor 26 to the power switch 14 located on the exterior of body portion 12 so that energy stored within the rechargeable battery can be selectively delivered to the motor by the user.

Figure 9:
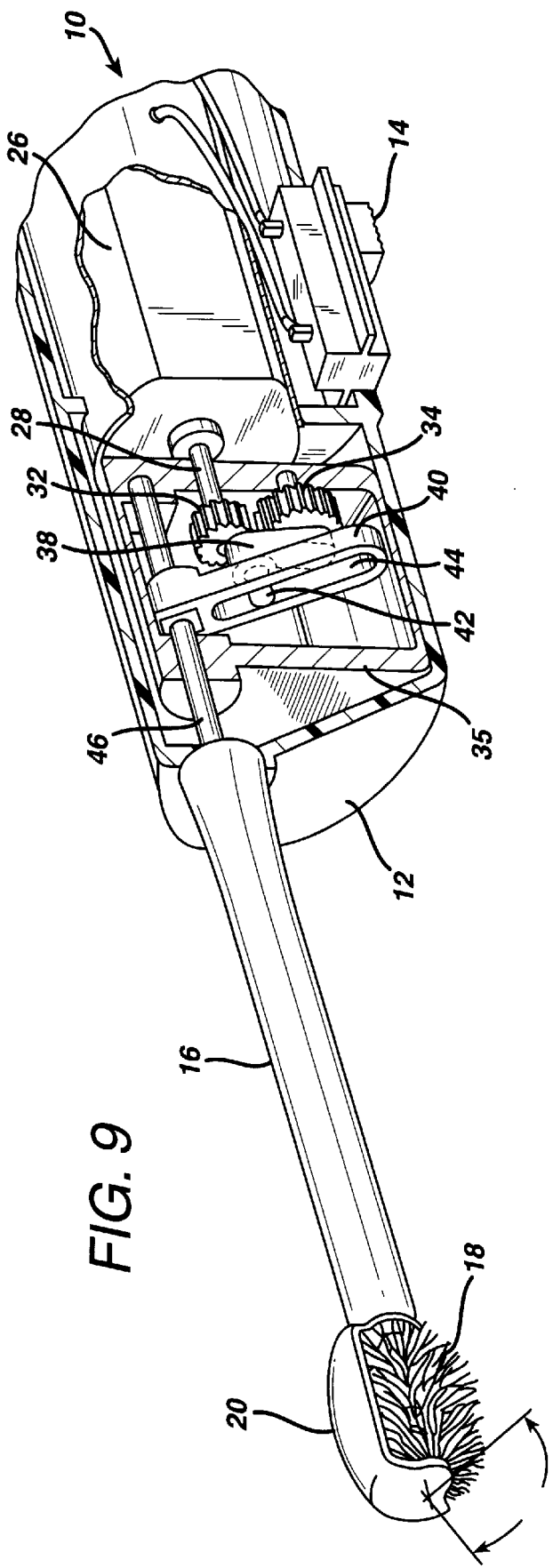
FIG. 9 is a perspective view in partial cross-section of the electric toothbrush of the subject invention illustrating the relationship between internal components of the toothbrush housed within the handle portion.

With continuing reference to FIGS. 2 and 3, in conjunction with FIG. 9, power from electric motor 26 is transferred from output shaft 28 to brush head 18 through a transmission assembly 30 which is supported within a transmission housing 35 disposed in the interior cavity 22 of body portion 12 adjacent the front end thereof. Transmission housing 35 essentially defines a sturdy support structure to maintain the various rotating components of the transmission assembly in proper alignment with respect to one another.

Figure 6:
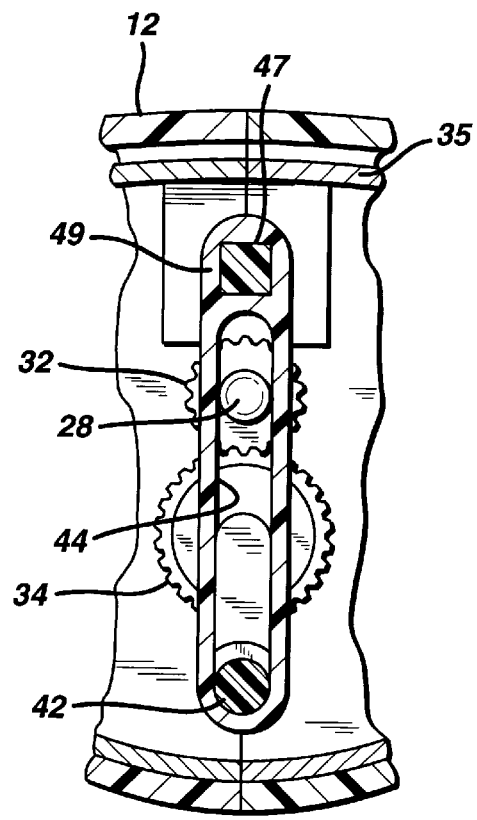
FIG. 6 is a cross-sectional view taken along line 6—6 of FIG. 3 illustrating the orientation of the components of the transmission assembly in a rest position.

As best seen in FIG. 9, transmission assembly 30 includes a gear train and a linkage sub-assembly. The gear train consists of a drive gear 32 mounted on the rotating output shaft 28 of electric motor 26 and a driven gear 34 mounted on a rotatable crank shaft 36. An upper journal port 37 is formed in the rear wall of transmission housing 35 to provide a bearing surface for output shaft 28, and a lower journal port 39 is formed in the rear wall of housing 35 to provide a bearing surface for crank shaft 36. The linkage sub-assembly consists of a crank 38 and a rocker arm 40. One end of crank 38 is mounted to crank shaft 36 so that it rotates therewith as gear 34 is driven by gear 32. The other end of crank 38 includes a slide pin 42 which is dimensioned and configured to engage and translate within an elongated slot 44 defined within rocker arm 40. Rocker arm 40 is mounted to an elongate rocker shaft 46 which is supported for rotation within front and rear rocker journals 45a and 45b formed in transmission housing 35. As best seen in FIG. 6, the connection between rocker arm 40 and rocker shaft 46 is facilitated by the engagement of rectangular locking block 47 within complementary aperture 49.

Figure 4:
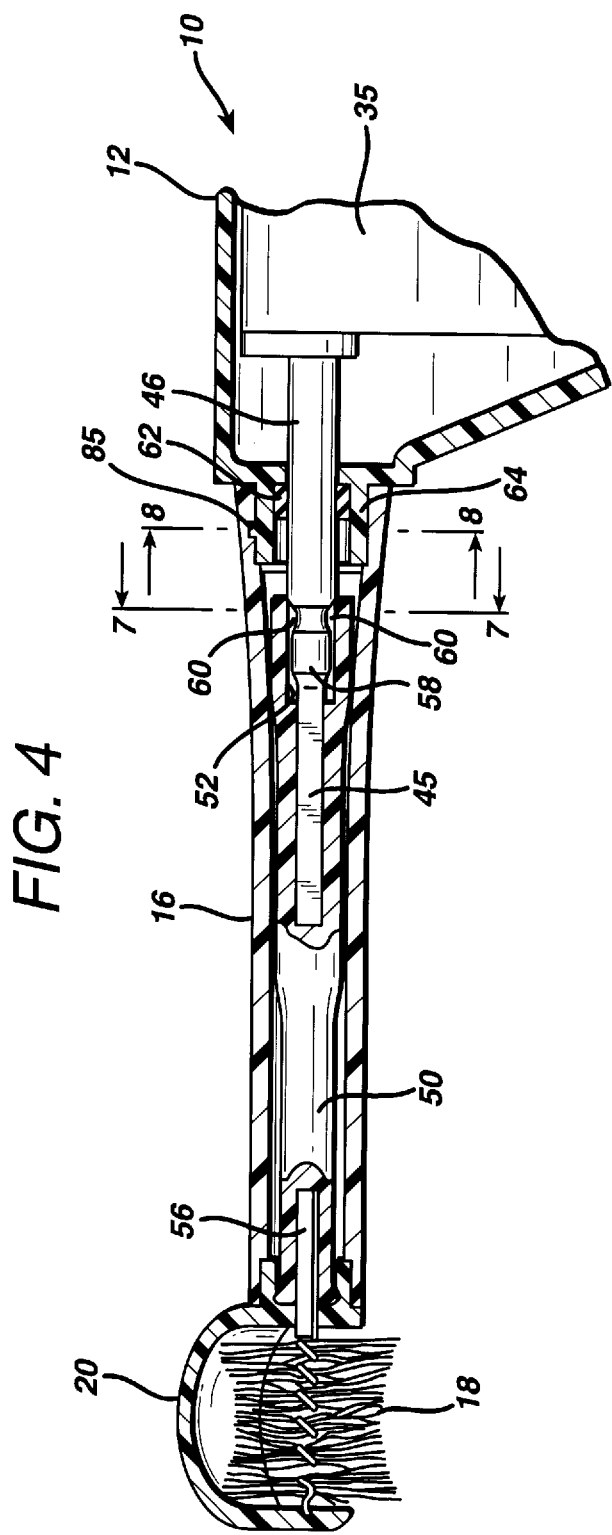
FIG. 4 is an enlarged side elevational view in cross-section of the detachable brush support housing of the electric toothbrush of FIG. 1.
Figure 5:
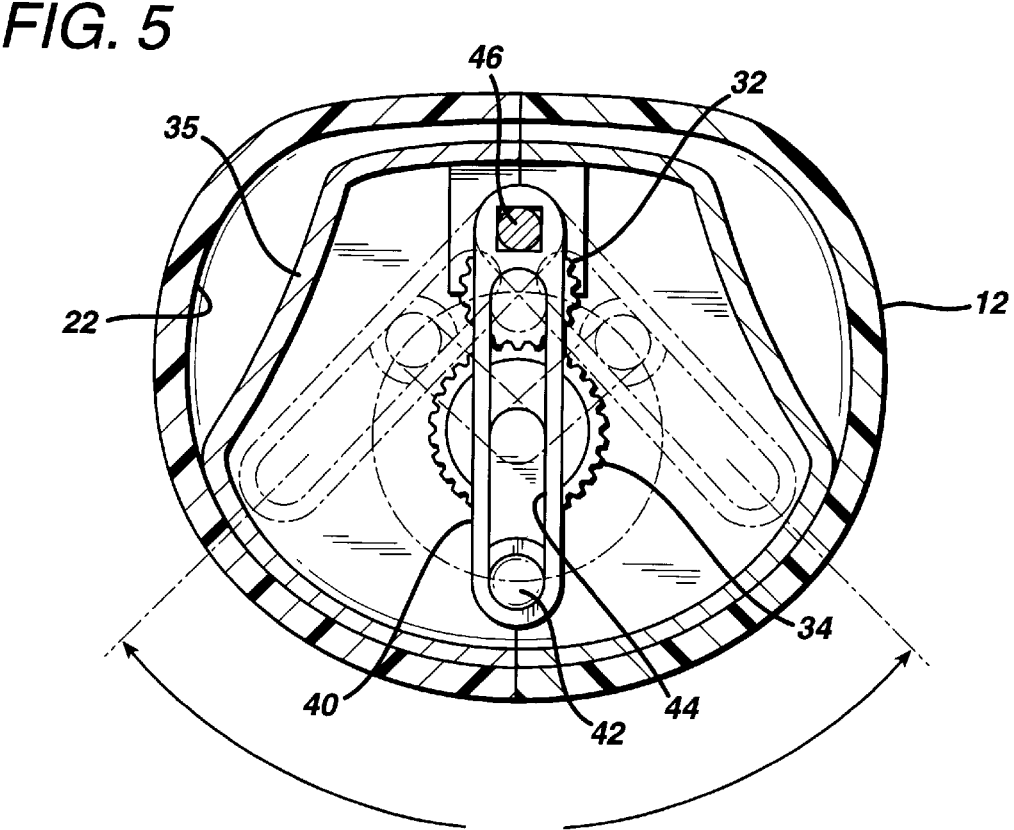
FIG. 5 is a cross-sectional view taken along line 5—5 of FIG. 3 illustrating the range of motion of the components of the transmission assembly housed within the handle portion of the electric toothbrush of the subject invention.

As illustrated in FIG. 5, in use, because the range of travel allotted to slide pin 42 within slot 44 is limited, continuous rotation of crank 38 within a 360° cycle causes corresponding reciprocating pendulum-like motion of rocker arm 40 within an angular sector of rotation of about 80° in a geometric plane which is perpendicular to the longitudinal axis of the rocker shaft. This pendulum-like motion is transferred directly to rocker shaft 46, which, in turn, is transferred to brush head 18 through an elongated brush shaft coupling 50 illustrated in FIG. 4.

Figure 7:
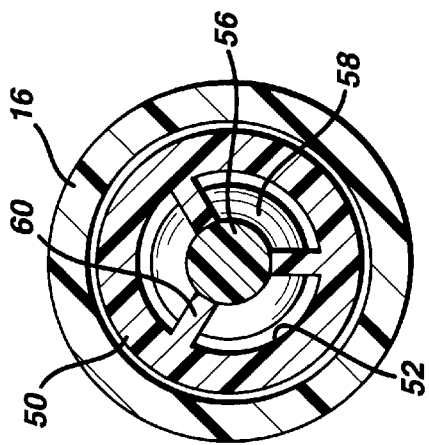
FIG. 7 is a cross-sectional view taken along line 7—7 of FIG. 4 illustrating the coupling engagement of the rocker shaft and the brush head drive shaft.

Referring to FIG. 4, brush shaft coupling 50 is supported within brush support housing 16 and is mounted to rotate therein about its longitudinal axis. An axial bore 52 extends partially through the rear end portion of shaft coupling 50 to accommodate rocker shaft 46. As best seen in FIG. 7, rocker shaft 46 is detachably supported within axial bore 52, through the provision of squared distal portion 45 and the detachable engagement of radially enlarged segment 58 by a plurality of circumferentially spaced apart radially inwardly projecting resilient fingers 60 defined within axial bore 52. The radial fingers serve to releasably engage a portion of the enlarged segment 58, securely retaining rocker shaft 46 so that the reciprocating motion of rocker arm 40 is directly transferred to brush shaft 56. The front end portion of shaft coupling 50 includes an axial bore 54 which extends partially therethrough to fixedly retain the brush head shaft 56. An annular bushing 62 is retained in the flanged mounting area 64 defined at the front end of body portion 12 to rotatably support rocker shaft 40 as it rotates.

Referring now to FIG. 10, there is illustrated three interchangeable brush support housings 70, 80 and 90, each having a particular brush head and shroud configuration, and each adapted to be detachably engaged to the flanged mounting area 64 at front end of the body portion 12 of powered toothbrush 10. Support housing 70 includes a generally spherical brush head 72 and a complementary hemi-spherical shroud 74 partially enclosing brush head 72. Support housing 80 includes a cylindrical brush head 82 with a radial concavity similar to brush head 18 and a complementary rectangular shroud 84 which partially encloses brush head 82. Support housing 90 contains a rearwardly tapered brush head 92 and a complementary rearwardly tapered shroud 94 which partially encloses brush head 92.

Figure 8:
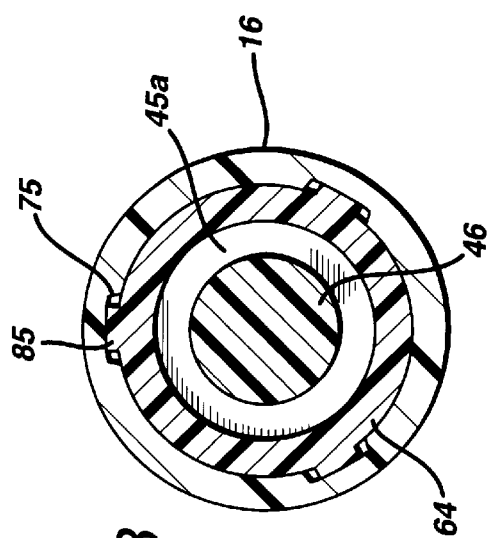
FIG. 8 is a cross-sectional view taken along line 8—8 of FIG. 4 illustrating the orientation of the connective engagement between the proximal end portion of the detachable brush support housing of the handle portion of the toothbrush.

As best seen in FIG. 8, the proximal end of each of the brush support housings illustrated in FIG. 10, as well as the brush support housing 16 discussed hereinabove, includes a plurality of spaced circumferentially apart engagement notches 75 formed within the interior bores thereof for receiving complementary engagement tabs 85 which project radially outwardly from the flanged mounting area 64 formed at the front end of body portion 12.

Although the electric toothbrush of the subject invention has been described with respect to a preferred embodiment, it will be readily apparent to those having ordinary skill in the art to which it appertains that changes and modifications may be made thereto without departing from the spirit or scope of the subject invention as defined by the appended claims.

What is claimed is:

1. An electric toothbrush comprising:
   a) an elongate body defining a handle and having an interior cavity formed therein;
   b) an elongate housing extending from a front end of the elongate body and supporting a brush head at a distal end thereof;
   c) an elongate drive shaft mounted for axial rotation within the elongate housing and connected to the brush head;
   d) an electric motor disposed within the interior cavity of the body and including a rotating output shaft; and
   e) a transmission assembly disposed within the interior cavity of the elongate body and including a crank arm, a follower attached to said crank arm, and a rocker arm having an elongate slot, said crank arm being operatively connected to said output shaft, said follower disposed in said elongate slot of said rocker arm, and said rocker arm being connected to said drive shaft, said transmission assembly converting rotational movement from said output shaft via said crank arm, follower, and rocker arm into reciprocating movement for said drive shaft and brush head about an axis of rotation shared commonly between them, and wherein said rocker arm has a reciprocating pendulum motion within an angular sector of rotation of approximately 80°.

* * * * *